United States Patent [19]

Kruse et al.

[11] Patent Number: 5,017,719

[45] Date of Patent: May 21, 1991

[54] ESTERS OF ARYLBISPERFLUOROALKYLCARBINOLS, AND A PROCESS FOR THE PREPARATION OF THESE COMPOUNDS

[75] Inventors: Alfred Kruse, Kelkheim; Günter Siegemund, Hofheim am Taunus; Ingo Ruppert, deceased, late of Bonn, all of Fed. Rep. of Germany, by Carl Horst Schroeder, administrator

[73] Assignee: Hoechst Aktiengesellschaft, Frankfurt am Main, Fed. Rep. of Germany

[21] Appl. No.: 225,547

[22] Filed: Jul. 28, 1988

[30] Foreign Application Priority Data

Aug. 5, 1987 [DE] Fed. Rep. of Germany ....... 3725941

[51] Int. Cl.$^5$ .............................................. C07C 69/76
[52] U.S. Cl. .................................................... 560/106
[58] Field of Search ........................................ 560/106

[56] References Cited

U.S. PATENT DOCUMENTS 3,236,894  2/1966  England .

FOREIGN PATENT DOCUMENTS 1210775  8/1966  Fed. Rep. of Germany .

OTHER PUBLICATIONS

Chem. Abstracts, vol. 82, 1975, No. 86321h.
Chem. Abstracts, vol. 95, 1981, No. 80415p.
Journal of the American Chemical Society, vol. 93, 1971, No. 5, pp. 2339–3341.
P. Gassmann et al., Tetrahedron Lett. 26, 5243–5246 (1985).
B. Farah et al., J. Org. Chem. 30, 998–1007 (1965).
Martin, J. C. et al., JACS 97(2), 6137–6144, 1975.

*Primary Examiner*—Paul J. Killos

[57] ABSTRACT

The invention relates to esters of the general formula IV

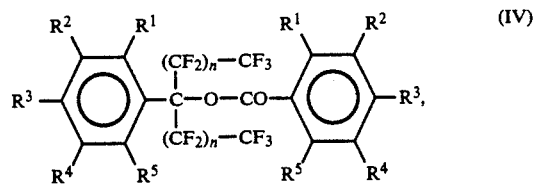

wherein $R^1$ to $R^5$ represent at least one of the substituents hydrogen, halogen, alkyl, alkoxy, alkylthio and perfluorinated alkyl, each having from 1 to 6 carbon atoms and n is 0 or an integer from 1 to 5.

The invention also relates to a process for the preparation of arylbisperfluoro alkyl compounds of the general formula VIII

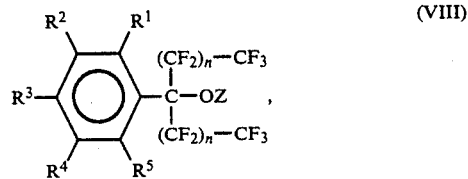

wherein $R^1$ to $R^5$ have the aforementioned meaning and Z means hydrogen or the aryl carbonyl group V

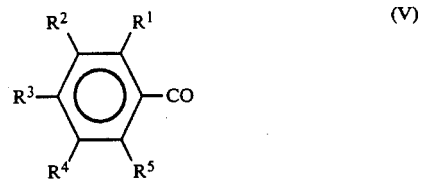

35 Claims, No Drawings

ESTERS OF ARYLBISPERFLUOROALKYLCARBINOLS, AND A PROCESS FOR THE PREPARATION OF THESE COMPOUNDS

The invention relates to esters of arylbisperfluoroalkylcarbinols, a process for their preparation and the preparation of the underlying arylbisperfluoroalkylcarbinols, i.e. of tertiary, fluorine-containing alcohols. The starting materials employed are arylcarboxylic acid halides or alternatively aryl perfluoroalkyl ketones, which by reaction with perfluoroalkyl halides in the presence of phosphorous acid triamides yield the arylcarboxylic acid esters of the arylbisperfluoroalkylcarbinols or, depending on the way in which the experiment is conducted, the carbinols themselves.

Arylbisperfluoralkylcarbinols are important intermediates in the preparation of plastics, inert fluids, medicaments and plant protection agents.

Arylbisperfluoroalkylcarbinols of the formula I can be produced by functionalization of the corresponding bisperfluoroalkyl ketones II or alternatively from aryl perfluoroalkyl ketones III (for formulae see formula sheet). In the two groups of the formula II, n can be identical or different and denotes 0 or an integer.

The most favorable preparation method for compounds having n=0 is the reaction according to Friedel-Crafts of the aromatic ring system with hexafluoroacetone II (n=0) with catalysis by a Lewis acid (J. Org. Chem. 30, 998-1007 (1965)). The position in which the hexa-fluoroisopropanol group is bonded to the aromatic ring is dependent on the nature and position of the substituents present, so that using this process only certain types of substitution of the fluorine-containing alcohols of the formula I can be obtained. Further disadvantages of this process are the possible formation of positional isomers on substitution on the aryl ring and purification problems caused by this, possible multiple substitution and also the fact that the resultant alcohols in some cases condense further in an undesired manner under the reaction conditions. The use of this process on the homologous ketones of hexafluoroacetone for the preparation of alcohols of the general formula I in which n denotes at least 1 gives significantly poorer yields (see German Patent No. 1,210,775).

If it is wished to introduce the perfluoroalkylcarbinol radical in a very specific position of the aromatic ring, a suitable aryl organometallic compound must first be synthesized and this must be adducted with the perfluorinated ketone in a second step (see German Patent No. 1,210,775).

The poor availability of the starting materials, namely the perfluoroalkyl ketones, and their toxicity are disadvantageous and limiting for both processes.

It is further known that alcohols of this type can also be prepared by introduction of a perfluoroalkyl radical into an aryl perfluoroalkyl ketone III by means of a suitable perfluoroalkyl organometallic compound (Tetrahedron Lett. 26, 5243-46 (1985)). The complicated preparation and lability of the perfluoroalkyl metal compound initially prepared and also the poor reproducibility of the published results (Tetrahedron Lett., 26, 5245, (footnote 4)) are disadvantageous here.

The invention relates to esters of arylbisperfluoroalkylcarbinols of the formula IV (see formula sheet) in which the radicals $R^1$ to $R^5$ are identical or different and are hydrogen, alkyl having 1 to 6 carbon atoms which can be perfluorinated, halogen, alkoxy or alkylthio each having 1 to 6 carbon atoms, and n is identical or different in both cases and denotes 0 or an integer from 1 to 5, and also to a process for their preparation and of the underlying carbinols, which comprises reacting carbonyl compounds of the general formula Va (see formula sheet) in which X is fluorine, chlorine, bromine or a perfluoroalkyl group $(CF_2)_nCF_3$, with perfluoroalkyl halides of the general formula $CF_3-(CF_2)_n-Y$ (VI) in which Y is chlorine, bromine or iodine and where n in each case has the meaning indicated, in the presence of an equimolar amount—relative to the compound Va—of phosphorous acid trisdialkylamides (in other words tris(dialkylamino)phosphines) of the general formula $P(N(alkyl)_2)_3$ (VII) to give the desired compounds of the formula VIII (see formula sheet), in which $R^1$ to $R^5$ and n have the meaning indicated and Z denotes hydrogen or the arylcarboxylic acid radical of the formula V (see formula sheet).

Under suitable reaction conditions in the reaction according to the invention, two perfluoroalkyl groups are transferred successively to the arylcarboxylic acid halides or one perfluoroalkyl group is transferred to an aryl perfluoroalkyl ketone which is also formed as an intermediate in the reaction with the aryl carboxylic acid halide. According to this embodiment, fluorinated alcohols having two different perfluoroalkyl groups can also be prepared.

The carboxylic acid halides, of which the carboxylic acid chlorides and fluorides are preferred, and the aryl perfluoroalkyl ketones can be unsubstituted or can carry one or more identical or different substituents $R^1$ to $R^5$ having a meaning other than hydrogen. Suitable substituents are, for example, alkyl, alkoxy and alkylthio radicals each having 1 to 6, in particular 1 to 3, carbon atoms, where the alkyl radicals can be perfluorinated, and also halogen (fluorine, chlorine, bromine and iodine).

Expediently, not more than three and preferably at most two substituents $R^1$ to $R^5$ having a meaning other than hydrogen are bonded to the aromatic ring. The alkyl, alkoxy and alkylthio substituents together expediently contain at most 4 carbon atoms and can be straight-chain or branched.

In general, the perfluoroalkyl halides used are compounds having 1 to 6, in particular 1 to 3, carbon atoms, preferably $CF_3Br$ and the homologous perfluoroalkyl iodides of the general formula $C_mF_{2m+1}I$ having m=1 to 6 or up to 3.

Suitable phosphorous acid trisdialkylamides (IV) are primarily the lower alkyl compounds, in particular those having $C_1-C_4$-alkyl, such as trisdimethylaminophosphine, trisdiethylaminophosphine and trisdipropyl- or isopropylaminophosphine; trisdiethylaminophosphine $P(N(CH_2CH_3)_2)_3$ is preferably used. This can be produced very simply in high yields by reaction of phosphorus trichloride with diethylamine in a solvent which is inert towards the reaction participants, for example an aliphatic, cycloaliphatic or aromatic hydrocarbon or a hydrocarbon mixture. The dialkylamino groups can contain identical or different alkyl groups.

In the reaction of the arylcarboxylic acid halide with a perfluoroalkyl halide under the influence of the phosphorous acid trisdialkylamide, formally one mole of halogen or mixed halogen is eliminated and a salt-like adduct is formed from the phosphorous acid triamide and halogen. The carboxylic acid halide is initially converted into an aryl perfluoroalkyl ketone in this manner.

This reaction has already been described in the earlier patent application Ser. No. 225,548 filed July 28, 1988, now U.S. Pat. No. 4,835,318. This ketone reacts further in the presence of an excess of phosphorous acid triamide and perfluoroalkyl halide with the adduction of a second perfluoroalkyl group and formation of the anion of the corresponding tertiary alcohol.

Thus if the carboxylic acid halide is brought to reaction with twice the molar amount of perfluoroalkyl halide and phosphorous acid triamide, the tertiary alcohols can be obtained directly from the initially resulting alcoholate of the formula IX (see formula sheet) after addition of an acid such as hydrogen fluoride, hydrogen chloride or hydrogen bromide gas. These gases can optionally also be dissolved in alcohols or water, the reaction expediently being kept above the temperature of formation of ice crystals when working with aqueous systems. However, this process gives unsatisfactory yields in some cases, so that it is sometimes more advantageous to prepare the tertiary alcohol from the corresponding ester by alkaline hydrolysis.

The esterification of the initially formed alcoholates using the carboxylic acid halide proceeds very smoothly, and the corresponding esters are obtained in high yields if the reaction is conducted in a suitable manner. By esterifying the tertiary alcoholates, the hydrolysis of the reaction mixture to release the alcohols can be avoided and the working up can be simplified. Furthermore, possible secondary reactions of the alcohols are prevented since the esters are chemically inert under the work-up conditions.

In order to introduce two different perfluoroalkyl radicals, the reaction expediently starts out from aryl perfluoroalkyl ketones. These are reacted with perfluoroalkyl halide and phosphorous acid triamide and the resulting alcoholate IX is converted into the carbinol by addition of an acid, as described above, or into the ester of the formula IV by further reaction with an arylcarboxylic acid halide Va.

The reaction of the arylcarboxylic acid halides or aryl perfluoroalkyl ketones with perfluoroalkyl halide in the presence of phosphorous acid triamide is in general carried out at temperatures from about $-100°$ C. to $+40°$ C. The short-chain perfluoroalkyl halides mostly react very rapidly at $-78°$ C. In the case of perfluoroalkyl halides having at least 2 carbon atoms, it is often necessary to increase the reaction temperatures in order to achieve rapid reaction; temperatures above $-40°$ C. and, for example, up to $+20°$ C. are then preferred. The duration of the reaction is known to be dependent on the other conditions, in particular the reaction temperature. The reaction is in general complete within a period from a few minutes up to several hours.

The reactions are in general carried out without use of overpressure. However, it can be expedient in individual cases, for example in the reaction of perfluoromethyl halides, to also work at elevated pressure, primarily if the reaction is carried out above the boiling point (at atmospheric pressure) of the perfluoroalkyl halide. In practice, the reaction is thus then carried out at least at the intrinsic pressure.

The present process is expediently carried out under anhydrous conditions in the presence of a solvent or diluent which is inert towards the reaction participants. Those which are primarily employed are aprotic liquids. For example, halogenated hydrocarbons such as methylene chloride or tetrachloroethane, nitriles, for example acetonitrile or its homologs or benzonitrile, esters such as diethyl carbonate or ethylene carbonate, and ethers such as tetrahydrofuran or dimethoxyethane are used. The solvent should be as anhydrous as possible.

During the entire duration of the reaction, it is advantageous to provide good intermixing of the batch, for example by stirring, and also to keep the salt-like intermediates and attendant products in solution by selection of a suitable solvent.

The process according to the invention can be carried out, for example, in such a way that solvents and diluents and two components are initially introduced and the third is metered in. To prepare the ester from the arylcarboxylic acid halide, it is favorable to initially introduce phosphorous acid triamide and perfluoroalkyl halide and to slowly add the carboxylic acid halide. Thus, a constant excess of reagents, relative to the carboxylic acid halide, is guaranteed at the beginning of the reaction, so that the intermediately formed ketone can immediately be further reacted to form the tertiary alcohol. This then reacts with further carboxylic acid halide under the reaction conditions present to give the ester. To prepare the tertiary alcohols from the aryl perfluoroalkyl ketones, the mode and the order of combination of the components is optional. However, subsequent addition of a protonic acid to the reaction mixture or hydrolysis of same is essential in each case, since otherwise a further reaction of the alcoholates with the phosphonium salts can occur.

For the two reactions described, the reagents are employed in an amount at least stoichiometric to the carbonyl compound, often in an excess up to 20%.

If the preparation of the fluorinated tertiary alcohols is started from carboxylic acid halides, a procedure can be used, for example, in which solvent or diluent, carboxylic acid halide and perfluoroalkyl halide are initially introduced and the phosphorous acid triamide is added as the last component. As can be seen from the stoichiometry of the reaction, the reagents here are now employed in at least twice the molar amounts in proportion to the carboxylic acid halide, an excess of up to 20% above the stoichiometric amount likewise being possible.

The working up of the reaction mixture advantageously takes place by distillative separation of the components. The working up of the esters, but not as a rule the alcohols, can often take place in a simpler manner and without problems by extraction, by separating them from simultaneously resulting phosphorous acid triamide/halogen adducts (in other words a phosphonium salt). In the case of addition of a non-polar solvent, for example a hydrocarbon such as hexane, to the reaction mixture, two phases are obtained, the perfluoroalkyl compound being in in the upper phase and the lower phase essentially containing the hydrocarbon-insoluble phosphonium salt as an attendant product.

Working up by extraction is not suitable for quantitative isolation of the alcohols. Rather, it is recommended to free the reaction mixture from solvent under reduced pressure and to treat the residue with water. The perfluoroalkyl compounds then separate out as the water-insoluble phase and can be purified after separation by distillation. This process is also suitable for isolation of the esters. The phosphonium salts can subsequently easily be reextracted from the aqueous phase on account of their good solubility in organic solvents, for example using a solvent such as $CH_2Cl_2$.

The structures of the compounds according to examples 1 to 10 and their physical data are summarized in the table.

EXAMPLES (1) 41 g (0.27 mol) of trifluoromethyl bromide were condensed into a solution of 31 g (0.25 mol) of benzoyl fluoride in 150 ml of $CH_2Cl_2$ at about $-70°$ C. in a round-bottomed flask with the exclusion of moisture. 62 g (0.25 mol) of phosphorous acid trisdiethylamide were then added. The mixture was stirred for 4 hours at about $-70°$ C. and then slowly warmed. After addition of the same volume of hexane to the reaction mixture, two phases formed. After phase separation, the lower phase was carefully extracted using hexane. The combined hexane phases were concentrated and distilled under reduced pressure. 35.1 g (81%) of 2-(1,1,1,3,3,3-hexafluoro-2-phenylpropyl) benzoate were obtained. Recrystallization from iso-propanol yielded colorless crystals.

(2) 45 g (0.3 mol) of trifluoromethyl bromide were condensed into a solution of 70 g (0.28 mol) of phosphorous acid trisdiethylamide in 150 ml of $CH_2Cl_2$ at about $-70°$ C. in a round-bottomed flask with the exclusion of moisture. 39 g (0.25 mol) of m-tolyl chloride in 50 ml of $CH_2Cl_2$ were then added dropwise at about $-70°$ C. during the course of 4 hours. The mixture was stirred for a further 3 hours at $-70°$ C. and then warmed. The reaction mixture was worked up as described in Example 1. 39 g (83%) of 2-(1,1,1,3,3,3-hexafluoro-2-(3-methylphenyl)propyl) 3-methylbenzoate were obtained. Recrystallization from iso-propanol yielded colorless crystals.

(3) 74 g (0.3 mol) of phosphorous acid trisdiethylamide in 150 ml of $CH_2Cl_2$ were initially introduced into a round-bottomed flask with the exclusion of moisture. At about 0° C., 74 g (0.3 mol) of pentafluoroethyl iodide were then metered in, then 44 g (0.25 mol) of o-chlorobenzoyl chloride in 50 ml of $CH_2Cl_2$ were slowly added dropwise. After 8 hours the mixture was warmed to room temperature. The reaction mixture was freed from solvent under reduced pressure and the residue was introduced into three times the volume of water. The organic phase was separated off, dried and distilled. 49 g (76%) of 3-(3-(2-chlorophenyl)-1,1,1,2,2,4,4,5,5,5-decafluoropentyl) 2-chlorobenzoate were obtained.

(4) to (10) The preparation of the compounds according to these examples, their structure, physical data and analysis values can be seen from the table, where R represents the indicated radical(s) $R^1$ to $R^5$ of the formula IV.

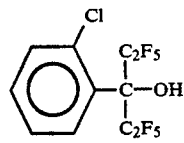
(11)

74 g (0.3 mol) of phosphorous acid trisdiethylamide in 150 ml of $CH_2Cl_2$ were initially introduced into a round-bottomed flask with the exclusion of moisture. 74 g (0.3 mol) of pentafluoroethyl iodide and 26.4 g (0.15 mol) of α-chlorobenzoyl chloride were added at about $-20°$ C. The mixture was warmed to 0° C. and stirred for about 8 hours at this temperature. 10 g of hydrogen chloride gas were then introduced, and the mixture was stirred for a further hour at 0° C. The reaction mixture was freed from solvent under reduced pressure and introduced into 3 times the volume of water. The organic phase was separated off, dried and distilled. 34.6 g (62%) of 3-(2-chlorophenyl)-1,1,1,2,2,4,4,5,5,5-decafluoropentan-3-ol of b.p. 66° C./2 mbar were obtained.

Analysis: Calc. C 34.89, H 1.33, Cl 9.36, F 50.18, Found C 35.1, H 1.2, Cl 9.7, F 50.0.

$^{19}F$-NMR($CDCl_3$): $-78.5$ (m, 3F, $CF_3$), $-120.3$ (m, 2F, $CF_2$)

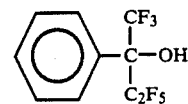

(a) Firstly, the starting material was prepared as follows: under protective gas, 35 g (0.25 mol) of benzoyl chloride in 150 ml of $CH_2Cl_2$ were initially introduced at about $-20°$ C. into a round-bottomed flask. 67 g (0.27 mol) of pentafluoroethyl iodide were firstly condensed in and 66.7 g (0.27 mol) of phosphorous acid trisdiethylamide were then metered in. The reaction mixture was subsequently stirred at 0° C. for a further 5 hours. After addition of the same volume of hexane to the reaction mixture, 2 phases formed. After phase separation, the lower phase was carefully extracted using hexane; the combined hexane phases were concentrated and distilled under reduced pressure. 20.8 g (58% yield) of pentafluoroethyl phenyl ketone of b.p. 76°-77° C./40 mbar were obtained.

(b) 56 g (0.25 mol) of pentafluoroethyl phenyl ketone in 150 ml of $CH_2Cl_2$ were initially introduced into a round-bottomed flask with the exclusion of moisture. At $-70°$ C., 46 g (0.3 mol) of trifluoromethyl bromide were condensed in and 74 g (0.3 mol) of phosphorous acid trisdiethylamide were added. The mixture was stirred for 5 hours at $-70°$ C. 15 g (0.4 mol) of hydrogen chloride gas were then introduced and the reaction mixture was slowly brought to room temperature. The solvent was evaporated under reduced pressure and the residue was introduced into three times the volume of water. The organic phase was separated off and distilled after drying. 41.1 g (56%) of 1,1,1,3,3,4,4,4-octafluoro-2-phenylbutan-2-ol of b.p. 66°-68° C./20 mbar were obtained as a colorless liquid.

Analysis: Calc. C 40.83, H 2.06, F 51.67, Found C 40.6, H 2.1, F 51.1.

$^{19}F$-NMR($CDCl_3$): $-74.5$ (m,3F,$CF_3$), $-78.8$ (m,3F,$CF_3-CF_2-$) $-121.3$ (m,2F, $CF_2$)

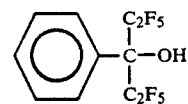

A solution of 8 g (0.2 mol) of sodium hydroxide in 40 g of water was added to a solution of 31.4 g (0.07 mol) of the ester from Example 4 in 50 ml of tetrahydrofuran in a round-bottomed flask. The mixture was heated under reflux with vigorous stirring for 90 minutes. After cooling, the mixture was acidified, and the organic phase was separated off and dried. Distillation of the organic phase yielded 17.1 g (71%) of 1,1,1,2,2,4,4,5,5,5-decafluoro-3-phenylpentan-3-ol of b.p. 78°-79° C./13 mbar as a colorless liquid.

TABLE

Examples 1-10

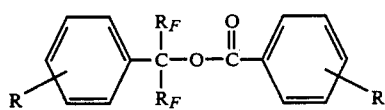

| Ex. | R | $R_F$ | Process analogous to example | Yield | Boiling point °C./mbar m.p. °C. | C (calc.) found | H (calc.) found | F (calc.) found | $^{19}$F-NMR[ppm] $CF_3$ | $^{19}$F-NMR[ppm] $CF_2$ | IR[cm$^{-1}$] C=O |
|---|---|---|---|---|---|---|---|---|---|---|---|
| 1 | H | $CF_3$ | | 81% | 96-97/0.1 m.p. 48-49 | (55.18) 55.0 | (2.89) 2.9 | (32.74) 32.7 | −70.5 | — | 1760 |
| 2 | 3-$CH_3$ | $CF_3$ | | 83% | 130-4/1 m.p. 58-59 | (57.45) 57.2 | (3.75) 3.8 | (30.29) 30.5 | −70.5 | — | 1755 |
| 3 | 2-Cl | $C_2F_5$ | | 76% | 132-4/0.1 | (41.81) 42.0 | (1.56) 1.4 | (36.74) 36.8 | −77.8 | −108.5 | 1770 |
| 4 | H | $C_2F_5$ | 3 | 51% | 111-2/0.2 | (48.23) 48.7 | (2.25) 2.4 | (42.38) 42.5 | 77.6 | −110.1 | 1765 |
| 5 | 3-$CH_3$ | $C_2F_5$ | 3 | 47% | 105-8/0.2 | (50.43) 50.7 | (2.96) 2.9 | (39.89) 40.2 | −77.6 | −110 | 1760 |
| 6 | 3,4$(CH_3)_2$ | $CF_3$ | 2 | 88% | 147-9/0.1 m.p. 77-79 | (59.41) 59.9 | (4.49) 4.8 | (28.19) 28.5 | −70.6 | — | 1755 |
| 7 | 3-O—$CH_3$ | $CF_3$ | 2 | 63% | 127-9/0.1 | (52.95) 53.5 | (3.46) 3.7 | (27.92) 27.5 | −70.4 | — | 1755 |
| 8 | 2-Cl | $CF_3$ | 2 | 87% | 112-4/0.1 m.p. 76 | (46.07) 46.2 | (1.93) 1.9 | (27.32) 27.4 | −69.3 | — | 1670 |
| 9 | 3-F | $CF_3$ | 2 | 48% | 90-3/0.3 | (48.99) 48.8 | (2.06) 2.1 | (38.74) 38.4 | −70.6 | — | 1765 |
| 10 | 3-F | $C_2F_5$ | 3 | 55% | 95-8/0.1 | (44.48) 44.4 | (1.66) 1.7 | (46.91) 47.4 | −77.5 | −110 | 1770 |

Formula sheet

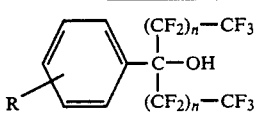 (I)

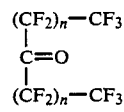 (II)

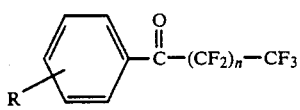 (III)

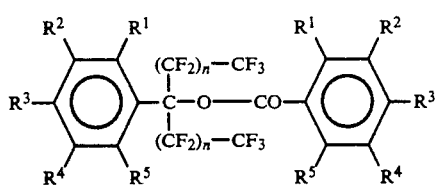 (IV)

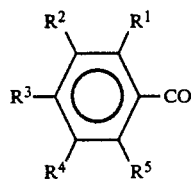 (V)

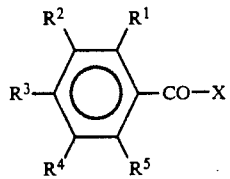 (Va)

-continued
Formula sheet $$CF_3-(CF_2)_n-Y \quad (VI)$$

$$P(N(Alkyl)_2)_3 \quad (VII)$$

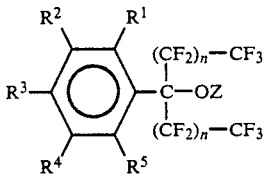 (VIII)

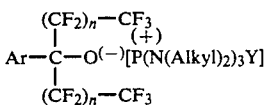 (IX)

We claim:

1. A process for the preparation of arylbisperfluoro alkyl compounds of the general formula VIII

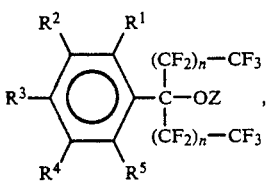 (VIII)

wherein $R^1$ to $R^5$ represent at least one of the substituents hydrogen, halogen, alkyl, alkoxy, alkylthio and perfluorinated alkyl, each having from 1 to 6 carbon atoms, n is 0 or an integer from 1 to 5 and Z represents hydrogen or the aryl carbonyl group V

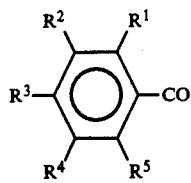

which comprises reacting a derivative of an aryl carbonyl compound having the general formula Va

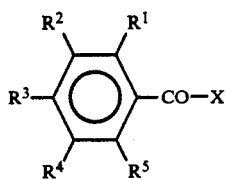

wherein $R^1$ to $R^5$ have the above-mentioned meaning and X represents fluorine, chlorine, bromine or a perfluoroalkyl group $-(CF_2)_nCF_3$, with a perfluoroalkyl halide of the general formula $CF_3-(CF_2)_n-Y$ (VI), wherein Y represents chlorine, bromine or iodine and n has the above-mentioned meaning, in the presence of a trisdialkyl amide of phosphorous acid of the general formula $P[N(alkyl)_2]_3$ (VII), the latter being present in an amount at least equimolar to compound Va.

2. A process as claimed in claim 1, wherein a compound Va, in which X represents fluorine, chlorine or bromine, is reacted with an equimolar amount of the perfluoroalkyl halide VI and the trisdialkyl amide of phosphorous acid VII to yield a compound VIII in which Z represents the aryl carbonyl group V.

3. A process as claimed in claim 1, wherein a compound Va in which X represents fluorine, chlorine or bromine, is reacted with an equimolar amount of the perfluoroalkyl halide VI and the trisdialkyl amide of phosphorous acid VII to yield a compound VIII in which Z represents the aryl carbonyl group V, and this compound is split by alkaline hydrolysis to yield a compound VIII, in which Z represents hydrogen.

4. A process as claimed in claim 1, wherein a compound Va in which X represents fluorine, chlorine or bromine, is reacted with double the molar amount of the perfluoroalkyl halide VI and the trisdialkyl amide of phosphorous acid VII and the resulting alcoholate is then split by addition of an acid to yield a compound VIII in which Z represents hydrogen.

5. A process as claimed in claim 1, wherein a compound Va in which X represents perfluoroalkyl is reacted with an equimolar amount of a perfluoroalkyl halide VI and a trisdialkyl amide of phosphorous acid VII and the resulting alcoholate is subsequently split by addition of an acid to yield a compound VIII in which Z represents hydrogen.

6. A process as claimed in claim 5, wherein the perfluoroalkyl group X is different from the perfluoroalkyl group in the perfluoroalkyl halide VI.

7. A process as claimed in claim 1, wherein X represents fluorine or chlorine.

8. A process as claimed in claim 1, wherein the perfluoroalkyl halide VI has from 1 to 3 carbon atoms.

9. A process as claimed in claim 8, wherein the perfluoroalkyl halide is $CF_3Br$.

10. A process as claimed in claim 1, wherein a perfluoro alkyl iodide is reacted.

11. A process as claimed in claim 1, wherein each alkyl in compound VII has from 1 to 4 carbon atoms.

12. A process as claimed in claim 11, wherein the trisdialkyl amide of phosphorous acid has the formula $P[N(CH_2CH_3)_2]_3$.

13. A process as claimed in claim 1, wherein the reaction is carried out at a temperature in the range of from $-100°$ C. to $+40°$ C.

14. A process as claimed in claim 13, wherein a perfluoroalkyl halide of at least 2 carbon atoms is reacted at a temperature above $-40°$ C.

15. A process as claimed in claim 14, wherein the reaction temperature is at most $+20°$ C.

16. A process as claimed in claim 1, which is carried out at a pressure not exceeding ambient pressure.

17. A process as claimed in claim 1, wherein a perfluoromethyl halide is reacted at a pressure higher than ambient pressure.

18. A process as claimed in claim 1, which is carried out under anhydrous conditions in the presence of a solvent or diluent inert towards the reactants.

19. A process as claimed in claim 18, wherein the solvent or diluent is an aprotic liquid.

20. A process as claimed in claim 1, wherein the perfluoroalkyl halide VI and the trisdialkylamide of the phosphorous acid $P[N(alkyl)_2]_3$ VII each are applied in an amount at least stoichiometric to the aryl carbonyl compound Va, and at most in an amount of 20% above the stoichiometric amount.

21. A process as claimed in claim 1, wherein one of the components Va, VI and VII is dosed into a mixture of the other two components and a solvent or diluent.

22. A process as claimed in claim 21, wherein the aryl carboxylic halide is dosed into a mixture comprising a perfluoroalkyl halide VI, a trisdialkyl amide of phosphorous acid VII and a solvent or diluent to yield a compound VIII in which Z represents the aryl carbonyl group V.

23. A process as claimed in claim 21, wherein a trisdialkylamide of phosphorous acid VII is added to a mixture comprising an aryl carboxylic halide Va, a perfluoroalkyl halide VI and a solvent or diluent to yield a compound VIII in which Z represents hydrogen.

24. A process as claimed in claim 1, wherein a compound VIII is produced in which Z represents the aryl carbonyl group V and this compound is separated by adding an unpolar solvent to the reaction mixture to yield a 2-phase system by which compound VIII is substantially separated from the by-products.

25. A process as claimed in claim 4, wherein a compound VIII is produced in which Z represents hydrogen and this compound is separated by subjecting the reaction mixture under reduced pressure to distillation, treating the residue with water and separating the insoluble compound V from the aqueous phase.

26. A process as claimed in claim 5, wherein a compound VIII is produced in which Z represents hydrogen and this compound is separated by subjecting the reaction mixture under reduced pressure to distillation, treating the residue with water, and separating the insoluble compound V from the aqueous phase.

27. Esters of the general formula

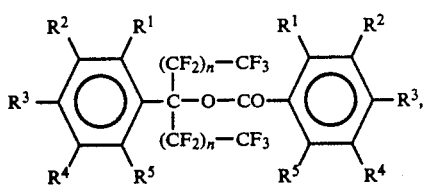 (IV)

wherein:

from one to three of the substituents $R^1$ to $R^5$ in each of the two phenyl groups represent substituents other than hydrogen, said substituents other than hydrogen being alkyl, alkoxy, alkylthio, or perfluorinated alkyl, each having 1 to 6 carbon atoms, or 2-chloro or fluorine, each of the groups $R^1$ to $R^5$ has the same meaning in each of the two phenyl groups, and n is 0 or an integer from 1 to 5.

28. Esters as claimed in claim 27, said esters having the general formula

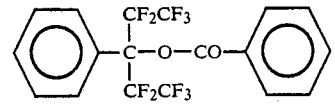

wherein n is 0 or an integer from 1 to 5, a is 1 or 2, and

R, which has the same meaning in each phenyl group, represents fluorine, $C_1$-$C_6$ alkyl, or $C_1$-$C_6$ alkoxy.

29. Esters as claimed in claim 28, wherein R is $C_1$-$C_6$ alkyl or $C_1$-$C_6$ alkoxy.

30. Esters as claimed in claim 29, wherein R is methyl or methoxy.

31. Esters as claimed in claim 27, wherein the substituents $R^1$ to $R^5$ contain altogether at most 4 carbon atoms.

32. Esters as claimed in claim 27, wherein n is 1.

33. Esters as claimed in claim 27, wherein one of $R^1$ to $R^5$ is fluorine.

34. Esters as claimed in claim 27, in which the alkyl, alkoxy, alkylthio and perfluorinated alkyl each have from 1 to 3 carbon atoms and n is 0 or an integer from 1 to 2.

35. An ester of the formula

* * * * *